(12) United States Patent
Aljuri et al.

(10) Patent No.: US 8,814,921 B2
(45) Date of Patent: Aug. 26, 2014

(54) TISSUE ABLATION AND CAUTERY WITH OPTICAL ENERGY CARRIED IN FLUID STREAM

(75) Inventors: Nikolai Aljuri, Hillsborough, CA (US); Rodney C. Perkins, Woodside, CA (US)

(73) Assignee: AquaBeam LLC, Woodside, CA (US)

( * ) Notice: Subject to any disclaimer, the term of this patent is extended or adjusted under 35 U.S.C. 154(b) by 978 days.

(21) Appl. No.: 12/399,585

(22) Filed: Mar. 6, 2009

(65) Prior Publication Data

US 2009/0227998 A1 Sep. 10, 2009

Related U.S. Application Data

(60) Provisional application No. 61/097,497, filed on Sep. 16, 2008, provisional application No. 61/034,412, filed on Mar. 6, 2008.

(51) Int. Cl.
| | | |
|---|---|---|
| *A61B 18/18* | (2006.01) | |
| *A61N 5/06* | (2006.01) | |
| *A61C 1/00* | (2006.01) | |
| *A61B 17/3203* | (2006.01) | |
| *A61C 17/02* | (2006.01) | |
| *A61B 18/20* | (2006.01) | |
| *A61B 18/24* | (2006.01) | |
| *A61B 17/00* | (2006.01) | |
| *A61B 18/00* | (2006.01) | |

(52) U.S. Cl.
CPC ..... *A61B 17/32037* (2013.01); *A61B 2018/206* (2013.01); *A61B 18/24* (2013.01); *A61B 2017/00274* (2013.01); *A61C 1/0046* (2013.01); *A61B 18/20* (2013.01); *A61C 17/0202* (2013.01); *A61B 2018/00547* (2013.01)

USPC .................. 607/88; 607/89; 607/91; 607/92; 607/93; 606/14; 606/15; 606/16

(58) Field of Classification Search
USPC ..................................... 606/2–19; 607/88–94
See application file for complete search history.

(56) References Cited

U.S. PATENT DOCUMENTS

| 3,818,913 A | 6/1974 | Wallach |
|---|---|---|
| 3,821,510 A | 6/1974 | Muncheryan |
| 3,847,988 A | 11/1974 | Gold |
| 3,875,229 A | 4/1975 | Gold |

(Continued)

FOREIGN PATENT DOCUMENTS

| CA | 2330436 | 11/1999 |
|---|---|---|
| DE | 9200447 U1 | 4/1992 |

(Continued)

OTHER PUBLICATIONS

European search report and opinion dated Nov. 7, 2011 for EP Application No. 09718273.7.

(Continued)

*Primary Examiner* — Ahmed Farah
*Assistant Examiner* — William Cheng
(74) *Attorney, Agent, or Firm* — Wilson Sonsini Goodrich & Rosati

(57) ABSTRACT

Methods and systems for modifying tissue use a pressurized fluid stream carrying coherent light energy. The methods and systems may be used for resecting and debulking soft and hard biological tissues. The coherent light is focused within a stream of fluid to deliver energy to the tissue to be treated.

38 Claims, 12 Drawing Sheets

(56) References Cited

U.S. PATENT DOCUMENTS

| | | | |
|---|---|---|---|
| 4,097,578 A | 6/1978 | Perronnet et al. | |
| 4,220,735 A | 9/1980 | Dieck et al. | |
| 4,239,776 A | 12/1980 | Glen et al. | |
| 4,377,584 A | 3/1983 | Rasmusson et al. | |
| 4,386,080 A | 5/1983 | Crossley et al. | |
| 4,461,283 A | 7/1984 | Doi | |
| 4,560,373 A | 12/1985 | Sugino et al. | |
| 4,636,505 A | 1/1987 | Tucker | |
| 4,760,071 A | 7/1988 | Rasmusson et al. | |
| 4,776,349 A | 10/1988 | Nashef et al. | |
| 4,913,698 A | 4/1990 | Ito et al. | |
| 5,037,431 A | 8/1991 | Summers et al. | |
| 5,116,615 A | 5/1992 | Gokcen et al. | |
| 5,135,482 A | 8/1992 | Neracher | |
| 5,207,672 A | 5/1993 | Roth et al. | |
| 5,257,991 A | 11/1993 | Fletcher et al. | |
| 5,267,341 A | 11/1993 | Shearin | |
| 5,322,503 A | 6/1994 | Desai | |
| 5,454,782 A | 10/1995 | Perkins | |
| 5,496,267 A | 3/1996 | Drasler et al. | |
| 5,505,729 A | 4/1996 | Rau | |
| 5,514,669 A | 5/1996 | Selman | |
| 5,562,703 A | 10/1996 | Desai | |
| 5,620,414 A | 4/1997 | Campbell, Jr. | |
| 5,630,794 A | 5/1997 | Lax et al. | |
| 5,649,923 A | 7/1997 | Gregory et al. | |
| 5,672,153 A | 9/1997 | Lax et al. | |
| 5,672,171 A | 9/1997 | Andrus et al. | |
| 5,753,641 A | 5/1998 | Gormley et al. | |
| 5,770,603 A | 6/1998 | Gibson | |
| 5,772,657 A | 6/1998 | Hmelar et al. | |
| 5,773,791 A | 6/1998 | Kuykendal | |
| 5,782,848 A | 7/1998 | Lennox | |
| 5,785,521 A | 7/1998 | Rizoiu et al. | |
| 5,817,649 A | 10/1998 | Labrie | |
| 5,836,941 A * | 11/1998 | Yoshihara et al. | 606/15 |
| 5,861,002 A | 1/1999 | Desai | |
| 5,871,462 A | 2/1999 | Yoder et al. | |
| 5,872,150 A | 2/1999 | Elbrecht et al. | |
| 5,902,499 A | 5/1999 | Richerzhagen | |
| 5,994,362 A | 11/1999 | Gormley et al. | |
| 6,022,860 A | 2/2000 | Engel et al. | |
| 6,066,130 A * | 5/2000 | Gregory et al. | 606/15 |
| 6,117,128 A | 9/2000 | Gregory | |
| 6,142,991 A | 11/2000 | Schatzberger | |
| 6,179,831 B1 | 1/2001 | Bliweis | |
| 6,200,573 B1 | 3/2001 | Locke | |
| 6,217,860 B1 | 4/2001 | Woo et al. | |
| 6,231,591 B1 | 5/2001 | Desai | |
| 6,254,597 B1 * | 7/2001 | Rizoiu et al. | 606/13 |
| 6,296,639 B1 | 10/2001 | Truckai et al. | |
| 6,378,525 B1 | 4/2002 | Beyar et al. | |
| 6,413,256 B1 | 7/2002 | Truckai et al. | |
| 6,425,877 B1 | 7/2002 | Edwards | |
| 6,451,017 B1 | 9/2002 | Moutafis et al. | |
| 6,565,555 B1 * | 5/2003 | Ryan et al. | 606/18 |
| 6,607,524 B1 | 8/2003 | LaBudde et al. | |
| 6,720,745 B2 | 4/2004 | Lys et al. | |
| 6,814,731 B2 | 11/2004 | Swanson | |
| 6,821,275 B2 | 11/2004 | Truckai et al. | |
| 6,890,332 B2 | 5/2005 | Truckai et al. | |
| 6,953,461 B2 | 10/2005 | McClurken et al. | |
| 6,960,182 B2 | 11/2005 | Moutafis et al. | |
| 6,986,764 B2 | 1/2006 | Davenport et al. | |
| 7,015,253 B2 | 3/2006 | Escandon et al. | |
| 7,122,017 B2 | 10/2006 | Moutafis et al. | |
| 7,163,875 B2 | 1/2007 | Richerzhagen | |
| 7,326,054 B2 | 2/2008 | Todd et al. | |
| 2001/0048942 A1 | 12/2001 | Weisman et al. | |
| 2002/0010502 A1 | 1/2002 | Trachtenberg | |
| 2002/0040220 A1 | 4/2002 | Zvuloni et al. | |
| 2002/0111617 A1 | 8/2002 | Cosman et al. | |
| 2002/0128637 A1 | 9/2002 | von der Heide et al. | |
| 2003/0060819 A1 | 3/2003 | McGovern et al. | |
| 2003/0065321 A1 | 4/2003 | Carmel et al. | |
| 2003/0073902 A1 | 4/2003 | Hauschild et al. | |
| 2003/0135205 A1 | 7/2003 | Davenport et al. | |
| 2005/0010205 A1 | 1/2005 | Hovda et al. | |
| 2005/0054994 A1 | 3/2005 | Cioanta et al. | |
| 2005/0165383 A1 | 7/2005 | Eshel et al. | |
| 2005/0256517 A1 * | 11/2005 | Boutoussov | 606/16 |
| 2005/0288639 A1 | 12/2005 | Hibner | |
| 2005/0288665 A1 | 12/2005 | Woloszko | |
| 2006/0129125 A1 | 6/2006 | Copa et al. | |
| 2006/0149193 A1 | 7/2006 | Hall | |
| 2006/0167416 A1 | 7/2006 | Mathis et al. | |
| 2006/0178670 A1 | 8/2006 | Woloszko et al. | |
| 2007/0025874 A1 | 2/2007 | Ophardt | |
| 2007/0129680 A1 | 6/2007 | Hagg et al. | |
| 2007/0278195 A1 | 12/2007 | Richerzhagen et al. | |
| 2008/0038124 A1 | 2/2008 | Kuehner et al. | |
| 2008/0082091 A1 * | 4/2008 | Rubtsov et al. | 606/17 |
| 2008/0097470 A1 | 4/2008 | Gruber et al. | |
| 2008/0154258 A1 | 6/2008 | Chang et al. | |
| 2008/0188868 A1 | 8/2008 | Weitzner et al. | |
| 2008/0221602 A1 | 9/2008 | Kuehner et al. | |
| 2008/0243157 A1 | 10/2008 | Klein et al. | |
| 2008/0249526 A1 | 10/2008 | Knowlton | |
| 2009/0018533 A1 | 1/2009 | Perkins et al. | |
| 2009/0060764 A1 | 3/2009 | Mitzlaff et al. | |
| 2009/0149712 A1 | 6/2009 | Fischer | |
| 2009/0157114 A1 | 6/2009 | Fischer et al. | |
| 2009/0227998 A1 | 9/2009 | Aljuri et al. | |
| 2009/0254075 A1 | 10/2009 | Paz et al. | |
| 2009/0287045 A1 | 11/2009 | Mitelberg et al. | |
| 2010/0145254 A1 | 6/2010 | Shadduck et al. | |
| 2011/0184391 A1 | 7/2011 | Aljuri et al. | |

FOREIGN PATENT DOCUMENTS

| | | |
|---|---|---|
| JP | 2003-000713 A | 1/2003 |
| WO | WO 98/18388 A1 | 5/1988 |
| WO | 92/10142 | 6/1992 |
| WO | WO 93/12446 A1 | 6/1993 |
| WO | 93/15664 | 8/1993 |
| WO | WO 97/29803 A1 | 8/1997 |
| WO | 99/56907 | 11/1999 |
| WO | WO 01/49195 A1 | 7/2001 |

OTHER PUBLICATIONS

International search report dated Mar. 31, 2011 for PCT/US2011/023781.

International search report and written opinion dated May 20, 2008 for PCT/US2008/050051.

Hillegersberg et al., "Water-jet-cooled Nd:YAG laser coagulation: selective destruction of rat liver metastases," Lasers Surg Med. 1991;11(5):445-454. [Abstract Only].

Sander et al., "Water jet guided Nd:YAG laser coagulation—its application in the field of gastroenterology," Endosc Surg Allied Technol. Aug. 1993;1(4):233-238. [Abstract Only].

Sander et al., "The water jet-guided Nd:YAG laser in the treatment of gastroduodenal ulcer with a visible vessel. A randomized controlled and prospective study," Endoscopy. Sep. 1989;21(5):217-220. [Abstract Only].

Botto et al., "Electrovaporization of the Prostate with the Gyrus Device," *J. Endourol.* (Apr. 2001) 15(3):313-316.

Stalder et al., "Repetitive Plasma Discharges in Saline Solutions," *Appl. Phys. Lett.* (Dec. 2001), 79(27):4503-4505.

Woloszko et al., "Plasma Characteristics of Repetitively-Pulsed Electrical Discharges in Saline Solutions Used for Surgical Procedures," (2002) *IEEE Trans. Plasma Sci.* 30(3):1376-1383.

Yang et al. "The Development of the Water Jet Scalpel With Air Pressure ," *Trans. ASME* (Jun. 2001), 123(2):246-248.

International Search Report and Written Opinion of PCT Application No. PCT/US2009/036390, dated Apr. 24, 2009, 11 pages total.

Richerzhagen et al., "Water Jet Guided Laser Cutting: a Powerful Hybrid Technology for Fine Cutting and Grooving," Proceedings of the 2004 Advanced Laser Applications Conference and Exposition, Ann Arbor, Michigan, Sep. 20-22, 2004, ALAC 2004, vol. 2, pp. 175-182; retrieved from the Internet: <http://www.synova.ch/pdf/ALAC04.pdf>.

(56) References Cited

OTHER PUBLICATIONS

U.S. Appl. No. 13/790,144, filed Mar. 8, 2013, Aljuri et al.
U.S. Appl. No. 13/790,218, filed Mar. 8, 2013, Aljuri et al.
U.S. Appl. No. 13/792,780, filed Mar. 11, 2013, Aljuri.
Office action dated Jan. 20, 2010 for U.S. Appl. No. 11/968,445.
Office action dated Mar. 5, 2008 for U.S. Appl. No. 11/968,445.
Office action dated Sep. 30, 2010 for U.S. Appl. No. 11/968,445.
Office action dated Oct. 5, 2009 for U.S. Appl. No. 11/968,445.
European search report and opinion dated Feb. 4, 2014 for EP Application No. 11740445.9.

* cited by examiner

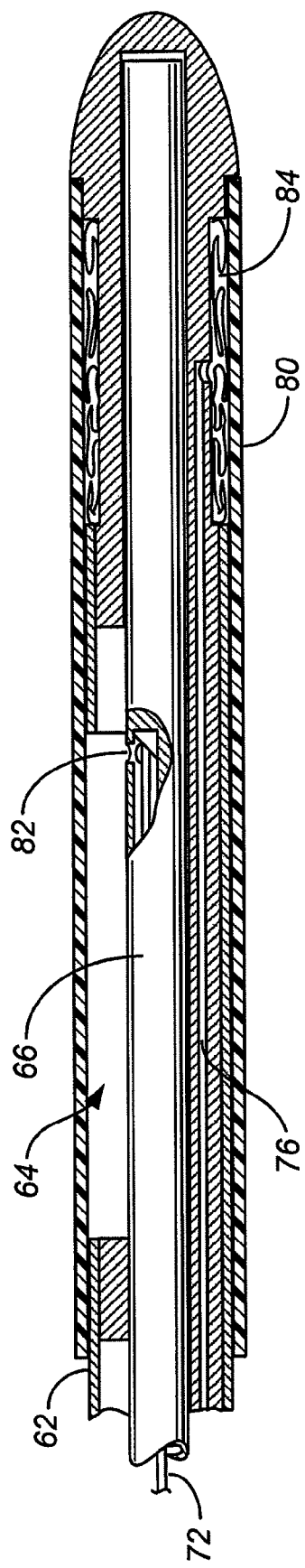
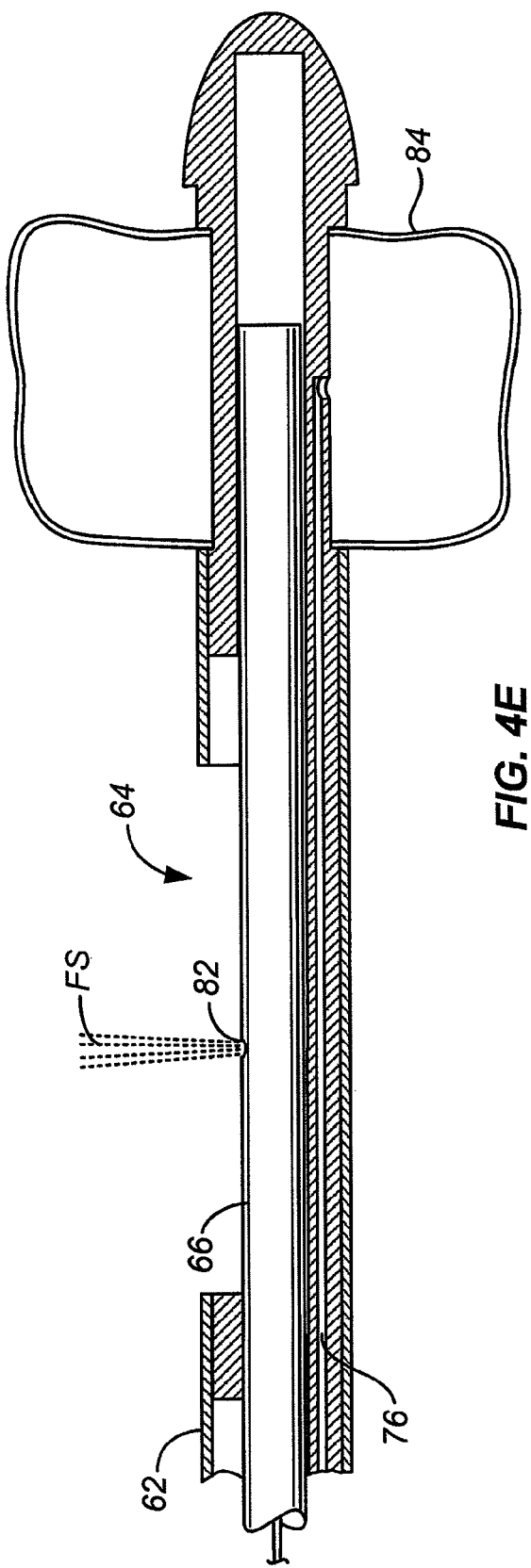
FIG. 4D
FIG. 4E

TISSUE ABLATION AND CAUTERY WITH OPTICAL ENERGY CARRIED IN FLUID STREAM

CROSS-REFERENCES TO RELATED APPLICATIONS

This application claims the benefit of provisional application No. 61/097,497, filed on Sep. 16, 2008, and of provisional application No. 61/034,412, filed on Mar. 6, 2008, the full disclosures of which are incorporated herein by reference. The subject matter of this application is related to that of commonly-owned application Ser. No. 11/968,445 which claimed the benefit of provisional application No. 60/883,097, filed on Jan. 2, 2007, the full disclosures of which are incorporated herein by reference.

BACKGROUND OF THE INVENTION

1. Field of the Invention

The present invention relates generally to medical methods and devices. In particular, the present invention relates to methods and devices for applying energy to ablate, cut, drill, or otherwise modify soft or hard tissues.

Both water jet technology and laser technology have been proposed for various tissue cutting and modification protocols. While each of these approaches has achieved commercial success, neither is ideally suited for all tissue modification protocols. For example, water jet or stream cutting alone does not cauterize tissue and therefore cannot prevent excessive bleeding. Furthermore, it can require very high pressure water delivery systems which can be difficult to control. Similarly, the use of lasers for modifying tissue can require very high energies, which can only be generated with large high power and expensive laser equipment. While laser technology can be effectively applied to cauterize tissue and stop bleeding, an extensive tissue zone of thermal damage is unavoidable. The consequences are the formation of edema and swelling of the treated tissue. With prostate tissue for example, tissue edema and swelling may result with the patient going into urinary retention requiring catheterization. Thus, improved energy-based methods and devices for ablating, cutting, drilling, and otherwise modifying tissues, would be desirable.

A number of medical conditions affect the male urethra causing a variety of symptoms including painful or difficult urination, a swollen prostate, blood in the urine, lower back pain, and the like. Some of these conditions, such as prostatitis, are bacterial infections which can be treated with antibiotics and other drugs. Other conditions, however, such as benign prostatic hyperplasia (BPH) and prostatic carcinoma, result in enlargement of the prostate and obstruction of the urethra, sometimes leading to complete loss of bladder function.

Both BPH and prostatic cancer require treatments which remove, resect, or shrink tissue in the prostate surrounding the urethra. Common treatments include transurethral resection of the prostate (TURP) where a resectoscope is placed in the urethra and used to remove excess prostatic tissue. Another procedure, referred to as transurethral incision of the prostate (TUIP), relies on cutting muscle adjacent to the prostate to relax the bladder opening to relieve difficulty in urination. More recently, a procedure referred to as transurethral needle ablation (TUNA) has been introduced where a needle is advanced through the urethra into the prostate and used to deliver energy, such as microwave, radiofrequency, or ultrasound energy, to shrink the size of the prostate, again relieving pressure on the urethra. Laser resection or ablation using transurethral optical fibers also finds use.

One minimally invasive laser resection protocol is photoselective vaporization of the prostate (PVP) where a laser beam with output powers ranging from 60 to 120 W is directed from the urethra against prostatic tissue to achieve irradiance (power density) levels over a certain volumetric power density, referred to as a vaporization threshold, below which tissue coagulation rather than vaporization occurs. As the irradiance level increases above the vaporization threshold, tissue vaporization increases and coagulation decreases. Lasers, even those having the highest possible beam quality, produce divergent beams. Therefore, the laser spot size enlarges with increasing probe distance from the tissue, and the power density decreases, reducing the rate of vaporization. Hence, in order to maximize the rate of tissue vaporization and thereby limit the extent of the zone of thermal damage characterized by tissue coagulation left after the procedure, the physician must steadily hold the fiber a fixed distance (e.g., 1-2 mm) away from the tissue and slowly scan the beam over the target tissue without varying the distance. Clearly, the effectiveness and duration of this procedure is highly dependent on the skill of the treating physician and the use of a high-power laser.

While generally successful, none of these methods are adequate to treat all patients and all conditions. In particular, patients having severe tissue intrusion into the urethral lumen resulting from BPH or prostatic cancer are difficult to treat with minimally invasive protocols which rely on tissue shrinkage rather than resection. Additionally, those treatments which resect tissue often cause substantial bleeding which can be difficult to staunch. Thus, many of these patients will eventually require conventional surgical resection or follow-up procedures to stop bleeding.

For these reasons, it would be desirable to provide alternative and improved tissue-modifying systems which rely on the application of energy from one or more sources to the tissue. In particular, it would be desirable to provide minimally invasive methods and devices which provide for enlarging the luminal area and/or volumetric resection of tissue surrounding the urethra. It would be particularly desirable if such methods and devices were transurethrally introduced and provided for rapid removal or destruction of such tissues surrounding the urethra where the removal or destruction products can be removed from the lumen to relieve pressure on the urethra, even where large volumes of tissue are being removed. It would be particularly desirable if the methods and devices allowed for controllable tissue resection and/or ablation depth from very shallow depths to several millimeters or deeper. It would also be advantageous if the ablation could simultaneously cauterize treated tissue to limit bleeding. It would also be desirable if the depth of residual coagulated tissue that remains after tissue ablation were minimized or completely eliminated. It would be a further advantage if the use of a high-power laser were not required. It would be particularly beneficial if the methods and devices allowed for rapid and controlling tissue ablation or resection which is less dependent on skill of the treating physician. Methods and devices for performing such protocols should present minimal risk to the patient, should be relatively easy to perform by the treating physician, and should allow for alleviation of symptoms with minimal complications and side effects even in patients with severe disease. At least some of these objectives will be met by the inventions described below.

2. Description of the Background Art

The use of water or other fluid jets as waveguides for carrying a laser beam for cutting and other manufacturing operations is described in U.S. Patent Application No. 2007/0278195, published Canadian application 2,330436 A1, PCT publication WO 99/56907, and U.S. Pat. Nos. 7,163,875; 5,902,499; and 5,773,791. U.S. Patent Application No. 2007/0025874 describes the use of laser fluid jets for disinfecting hands. The use of lasers for cutting biological tissue is described in U.S. Patent Application No. 2002/0128637 and for ablating prostate tissue is described in U.S. Pat. Nos. 5,257,991; 5,514,669; and 6,986,764. Use of a transurethral endoscope for bipolar radiofrequency prostate vaporization is described in Boffo et al. (2001) *J. Endourol.* 15:313-316. Pressurized water streams for effecting surgical incisions are described in U.S. Pat. Nos. 7,122,017 and 5,620,414, and for drilling teeth are described in U.S. Pat. Nos. 7,326,054. 5,785,521 and 6,607,524 describe the use of laser energy to cause thermo-elastic failure and fracture of hard biological materials combined with water/air technology to cool and remove (or further fracture) the already fractured material and debris from the treatment site. Radiofrequency discharge in saline solutions to produce tissue-ablative plasmas is discussed in Woloszko et al. (2002) *IEEE Trans. Plasma Sci.* 30:1376-1383 and Stalder et al. (2001) *Appl. Phys. Lett.* 79:4503-4505. Air/water jets for resecting tissue are described in Jian and Jiajun (2001) *Trans. ASME* 246-248. US2005/0288639 described a needle injector on a catheter based system which can be anchored in a urethra by a balloon in the bladder. U.S. Pat. Nos. 6,890,332; 6,821,275; and 6,413,256 each describe catheters for producing an RF plasma for tissue ablation. Other patents and published applications of interest include: U.S. Pat. Nos. 7,015,253; 6,953,461; 6,890,332; 6,821,275; 6,451,017; 6,413,256; 6,378,525; 6,296,639; 6,231,591; 6,217,860; 6,200,573; 6,179,831; 6,142,991; 6,022,860; 5,994,362; 5,872,150; 5,861,002; 5,817,649; 5,770,603; 5,753,641; 5,672,171; 5,630,794; 5,562,703; 5,322,503; 5,116,615; 4,760,071; 4,636,505; 4,461,283; 4,386,080; 4,377,584; 4,239,776; 4,220,735; 4,097,578; 3,875,229; 3,847,988; US2002/0040220; US2001/0048942; WO 93/15664; and WO 92/10142.

BRIEF SUMMARY OF THE INVENTION

Methods, devices, and systems according to the present invention provide for delivery of coherent light and fluid energy to ablate, resect, drill, cut, or otherwise modify tissue. The tissues to be treated can be soft tissue, such as muscle, organ tissue, nerve tissue, cerebral tissue, skin tissue, glandular tissue or the like, or can be hard tissue, such as tooth, bone, cartilage, or the like. Particular treatments include ablation, such volumetric tissue ablation where volumes or regions of the tissue are vaporized, shrunk, necrosed or the like. The tissue modification can also be cutting where the tissue is severed into pieces or regions along a resection plane, or can be drilling where a hole is formed into the tissue, such as drilling into a tooth, or the like.

The present invention is particularly intended for treating/modifying soft and hard biological tissue. Depending on the power levels, treatment times, and treatment patterns selected, the present invention can provide for tissue resection, e.g. cutting along a line of tissue; tissue volume reduction; tissue surface modification; and the like. A particular advantage of the present invention arises from the simultaneous delivery of both fluid energy (constant or pulsating) in the form of a pressurized liquid medium and coherent light energy which will be propagated with constant power density through the fluid medium by total internal reflection thereby eliminating the need of laser focus-distance control. Where the pressurized fluid medium is principally relied on for cutting or tissue ablation, the coherent light can be delivered at an energy level selected to provide cauterization, i.e. the staunching of bleeding which would otherwise occur as a result of the tissue resection or ablation. Alternatively, by using higher coherent light energy levels, the coherent light can work together with the pressurized fluid stream to achieve faster, deeper, or otherwise enhanced cutting, tissue volume reduction, or other tissue modifications with significantly diminished laser power requirements as compared to current treatments such as photoselective vaporization of the prostate (PVP).

Specific prostate treatments according to the present invention comprise positioning a coherent light and fluid energy source within the urethra and directing a fluid stream carrying the energy radially outwardly from the energy source toward the urethral wall within the prostate. The fluid stream will usually be moved relative to the urethra to remove a predefined volume of prostate tissue surrounding the urethral lumen in order to partially or fully relieve the compression and/or obstruction. In other embodiments, the treatments of the present invention may be combined with chemotherapy and other forms of drug delivery, as well as treatment with external X-ray and other radiation sources and administration of radiopharmaceuticals comprising therapeutic radioisotopes. For example, one or more drugs may be combined with the saline or other fluid which is being delivered. The combination liquid/coherent light delivery can be used to both resect tissue and wash the tissue away while leaving intraprostatic blood vessels, capsule, and sphincter muscle undamaged.

Benefits of the high pressure liquid/light energy source include reduced or no bleeding with reduced or no need for cauterization and decreased risk of perforating or otherwise damaging the capsule of sphincter muscles. Alternatively, the device which is used to position the fluid/light energy source can be utilized to separately deliver a desired chemotherapeutic or other drug (as just set forth), either before, during, or after energy treatment according to the present invention. While the present invention is specifically directed at transurethral treatment of the prostate, certain aspects of the invention may also find use in the treatment of other body lumens, organs, passages, tissues, and the like, such as the ureter, colon, esophagus, lung passages, bone marrow, and blood vessels.

Thus, in a first aspect of the present invention, methods for modifying tissue comprise generating a stream of a light transmissive fluid medium, such as saline, water, alcohol, liquefied $CO_2$ and other liquefied gases (gases which are liquids at the pressure and temperature of use), fluid containing drug compounds such as vasocontricting agents (to reduce bleeding) and/or anesthetic agents (to reduce pain) and/or anti-inflammatory agents, antibiotics (to reduce infection), or the like. A source of coherent light, such as a laser, is coupled to the light transmissive medium through a waveguide or other optical coupler so that light is transmitted through said stream by total internal reflection. The fluid stream which carries the coherent light is then directed at target tissue, such as within the prostate.

While a particular advantage of the present invention is the simultaneous delivery of a pressurized fluid stream and laser or other optical energy, in some instances either the fluid stream or the optical energy may be delivered alone. For example, it may be desirable to deliver the fluid stream without optical energy to perform conventional water jet resection or volume reduction of tissue. After such water jet treatment, the optical energy can be added to cauterize and/or perform a procedure at a higher total energy. Optionally, the pressure, volume, flow velocity, temperature, or other characteristics of the fluid stream may be varied depending on whether optical energy is present, e.g., cauterization may be performed at lower pressures than tissue resection. In all cases the removed tissue and/or remaining tissue can be used for histological evaluation or other diagnostic procedures. It is a particular advantage that the removed tissue has not been vaporized or otherwise damaged to the extent it is with PVP and the subsequent analysis is impaired.

The liquid stream may be generated in a variety of ways, typically being delivered under pressure through a nozzle, where the nozzle typically has an area in the range from 0.0005 $mm^2$ to 5 $mm^2$, usually from 0.02 $mm^2$ to 0.2 $mm^2$, and the pressure is in the range from 10 psi to 1000 psi, typically from 50 Psi to 500 Psi. The light which is coupled into the light transmissive fluid will typically have a power level in the range from 10 mW to 40 W, typically from 100 mW to 10 W. Suitable laser sources include solid state lasers. For treating prostate tissue, the stream will be directed radially outward from a location in the urethra within the prostate.

Typically, prostate treatment will comprise positioning a probe within the urethra, directing the pressurized stream of light transmissive liquid medium radially outward from the probe to the prostate tissue surrounding the urethra. The coherent light is focused within the stream of liquid medium as the stream is directed at the prostate tissue. In this way, tissue volume reduction of the prostate may be efficiently carried out, while the coherent light can provide cauterization with minimal laser power to reduce the bleeding associated with the treatment.

In a second aspect of the present invention, a system for delivering laser or other coherent light energy to tissue comprises a tissue probe, a fluid nozzle on the probe, and a waveguide disposed within the probe. The tissue probe is suitable for introducing into solid tissue, tissue lumens, body cavities, or the like. In the exemplary embodiment, the tissue probe is suitable for transurethral introduction into the prostate so that a distal end of the probe is positioned within the prostate. A nozzle is provided for emitting a stream of light transmissive fluid, and a waveguide transmits coherent light into the fluid so that the fluid acts as a guide for further directing the coherent light to the tissue for treatment. Usually, the tissue probe will be adapted to be advanced through the urethra, but a wide variety of other specific designs would also be available for delivery into solid tissue, body lumens, or body cavities. Probes of the present invention typically have at least one central axial passage for delivering the light transmissive fluid to the nozzle, and the nozzle is typically disposed on the probe to deliver the fluid radially outwardly (laterally) under pressure.

In an exemplary embodiment, the probe comprises an outer tube having an axial lumen and an inner fluid delivery tube reciprocally mounted in the axial lumen. A central axial passage is disposed in the inner fluid delivery tube, and the waveguide is disposed in the central axial passage. In this way, the light transmissive fluid can be delivered through the central axial passage and diverted outwardly through the nozzle. The waveguide would be disposed to deliver coherent light through the central axial passage and to reflect or otherwise divert the light radially so that it is focused within the light transmissive fluid being delivered through the nozzle. By focusing the energy as it is emanating from the tissue probe, the light will be delivered through the fluid stream to assist in propagation.

In the specific embodiments, the distal end of the inner fluid delivery tube is disposed adjacent to a window in the outer tube. The inner tube may then be reciprocated and/or rotated relative to the outer tube so that the fluid stream and coherent light emanating from the inner fluid delivery tube may be delivered into tissue adjacent to or surrounding the outer tube through the window.

BRIEF DESCRIPTION OF THE DRAWINGS

FIGS. 4A-4E illustrate an alternative design for the tissue debulking device of the present invention, illustrating specific components and features for delivering fluids, inflating balloons, rotating and reciprocating the fluid and light delivery mechanism, and the like.

DETAILED DESCRIPTION OF THE INVENTION

Figure 1:
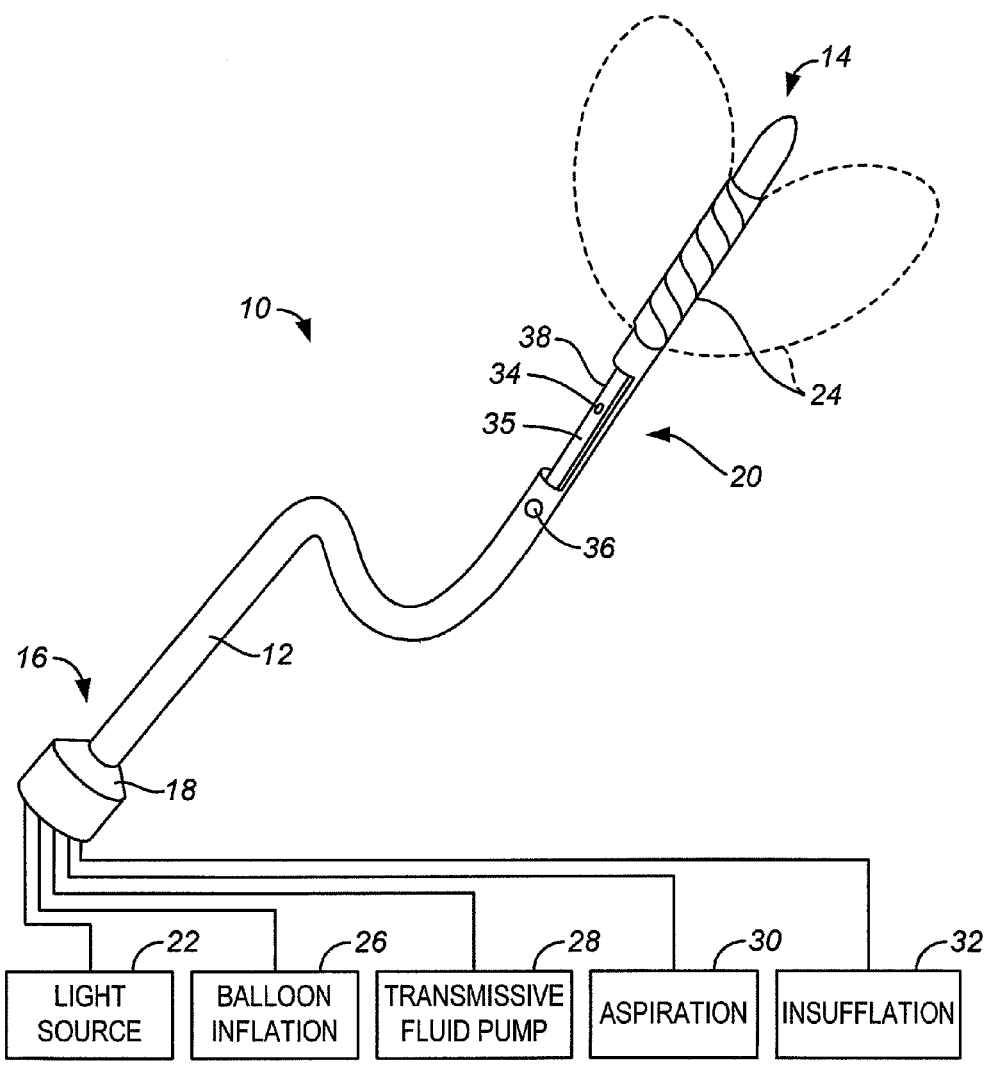
FIG. 1 is a schematic illustration of a device suitable for performing intraurethral prostatic tissue debulking in accordance with the principles of the present invention.

Referring to FIG. 1, an exemplary prostatic tissue debulking device 10 constructed in accordance with the principles of the present invention comprises a catheter assembly generally including a shaft 12 having a distal end 14 and a proximal end 16. The shaft 12 will typically be a polymeric extrusion including one, two, three, four, or more axial lumens extending from a hub 18 at the proximal end 16 to locations near the distal end 14. The shaft 12 will generally have a length in the range from 15 cm to 25 cm and a diameter in the range from 1 mm to 10 mm, usually from 4 mm to 8 mm. The shaft will have sufficient column strength so that it may be introduced upwardly through the male urethra, as described in more detail below.

The shaft will include a fluid/coherent light energy source 20 positioned near the distal end 14 of the shaft 12. The source 20, in turn, is connected to an external light source 22 and light transmissive fluid source 28. Distal to the energy source 20, an inflatable anchoring balloon 24 will be positioned at or very close to the distal end 14 of the shaft. The balloon will be connected through one of the axial lumens to a balloon inflation source 26 connected through the hub 18. In addition to the light source 22, fluid pump 28, and balloon inflation source 26, the hub will optionally further include connections for an aspiration (a vacuum) source 30, and/or an insufflation (pressurized $CO_2$ or other gas) source 32. In the exemplary embodiment, the fluid pump 28 can be connected through an axial lumen (not shown) to one or more port(s) 34 on an inner fluid delivery tube 35. The aspiration source 30 can be connected to a window or opening 38, usually positioned proximally of the energy source 20, while the insufflation source 32 can be connected to a port 36 formed in the wall of shaft 12. The energy will be directed through the window 38 as described in more detail below.

Figure 2:
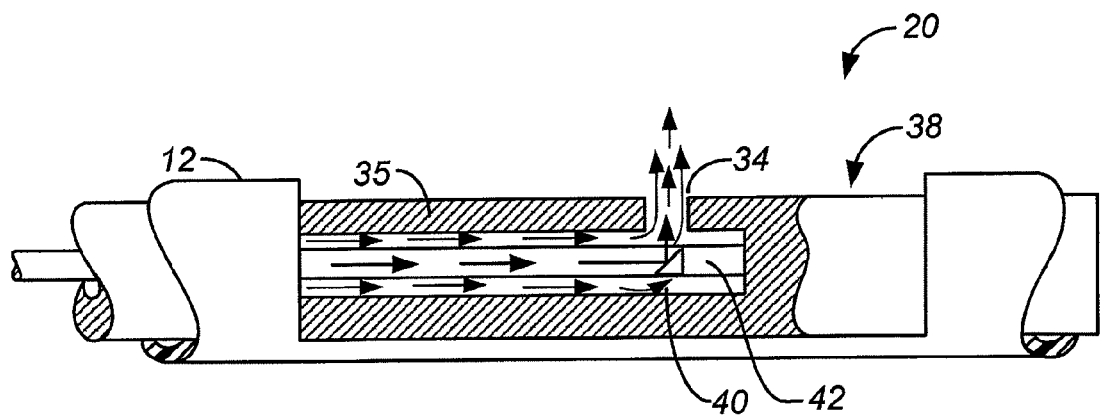
FIG. 2 is a detailed illustration of the pressurized fluid/coherent light delivery mechanism used in the device of FIG. 1.

Referring now to FIG. 2, the fluid/coherent light energy source 20 is defined by window 38 in the wall of shaft 12. The inner fluid delivery tube 35 is reciprocatably and rotatably mounted within a central lumen of the shaft 12 so that the port 34 may be rotated and/or axially advanced and retracted within the window relative to the shaft. The inner fluid delivery tube 35 has a central passage 40 which is attachable to the transmissive fluid pump 28 through the hub 18 to carry the transmissive fluid under pressure and emit a fluid or jet stream through the port 34 in a lateral direction. An optical waveguide 42 is also positioned within the central passage 40 of the inner fluid delivery tube 35.

Figure 2A:
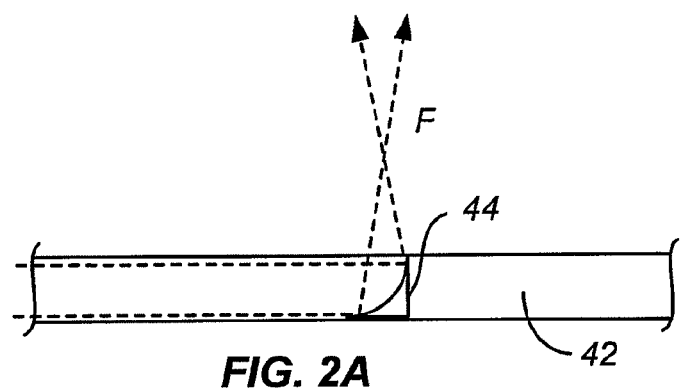
FIGS. 2A and 2B illustrate two alternative arrangements for focusing coherent light from a waveguide into a pressurized liquid stream in the mechanism of FIG. 2.
Figure 2B:
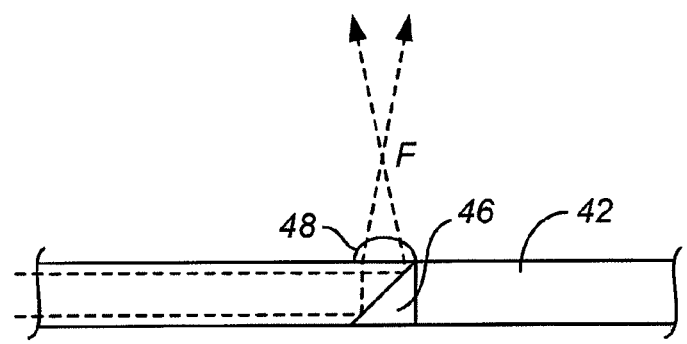

As shown in FIGS. 2A and 2B, the light transmissive fiber 42 includes an element 44 (FIG. 2A) or 46 (FIG. 2B) for transversely or laterally reflecting light transmitted through the fiber so that it may be emitted through the port 34 and into the flowing fluid stream passing therethrough. It will be desirable that the light emitted from the optical waveguide 42 be focused at a point F within the flowing fluid stream so that the light may then be transmitted and propagated through the stream by total internal reflection. Reflective element 44 may have a parabolic or other shaped surface to effect the desired focusing. In contrast, the reflective element 46 may have a flat, non-focusing surface that passes the light through a focusing lens 48, as shown in FIG. 2B.

Figure 3A:
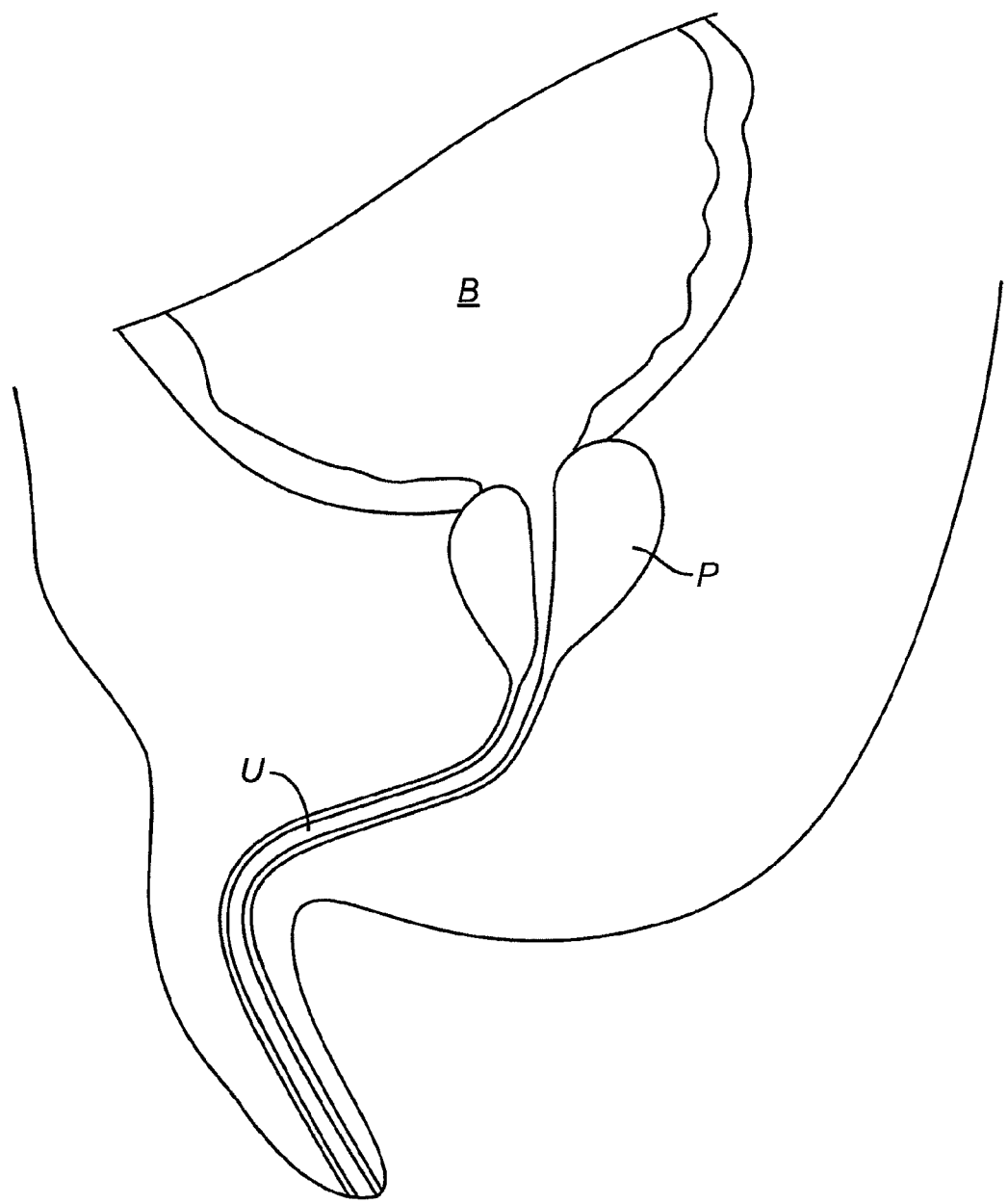
FIGS. 3A-3C illustrate use of the device of FIG. 1 in performing prostatic tissue debulking.
Figure 3B:
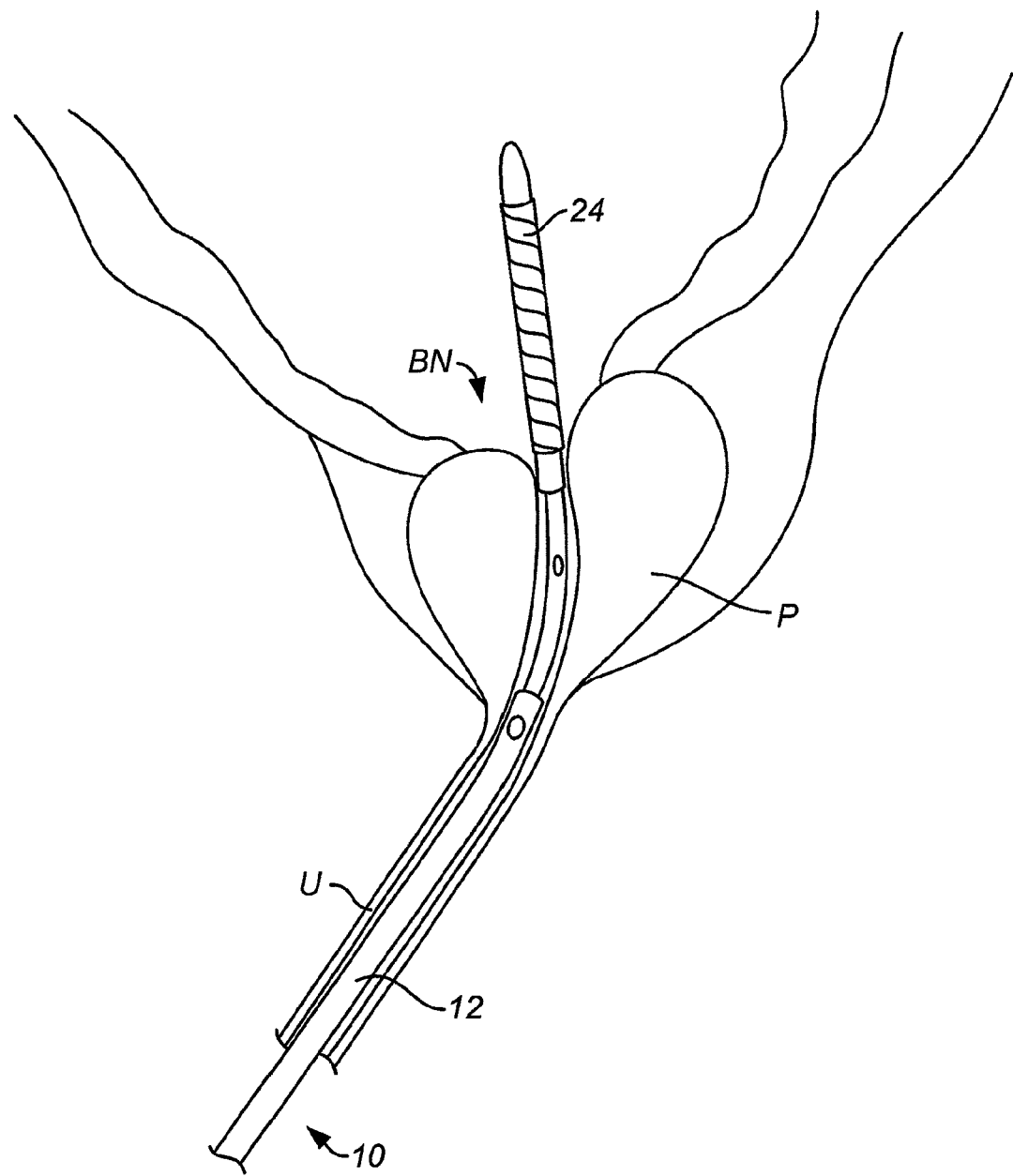
Figure 3C:
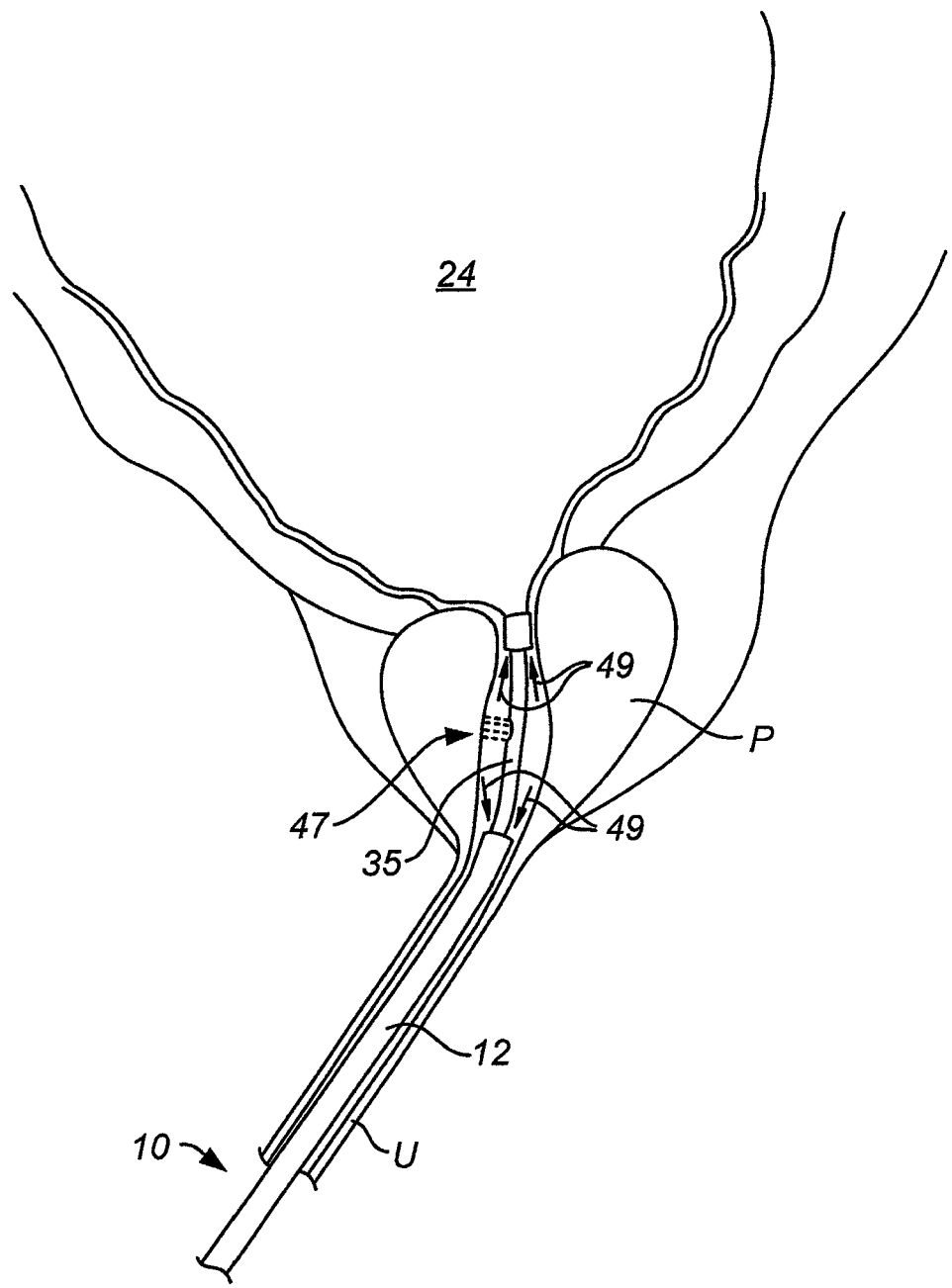

Referring now to FIGS. 3A-3C, the prostatic tissue debulking device 10 is introduced through the male urethra U to a region within the prostate P which is located immediately distal to the bladder B. The anatomy is shown in FIG. 3A. Once the catheter 10 has been positioned so that the anchoring balloon 24 is located just distal of the bladder neck BN (FIG. 3B) the balloon can be inflated, preferably to occupy substantially the entire interior of the bladder, as shown in FIG. 3C. Once the anchoring balloon 24 is inflated, the position of the prostatic tissue debulking device 10 will be fixed and stabilized within the urethra U so that the energy source 20 is positioned within the prostate P. It will be appreciated that proper positioning of the energy source 20 depends only on the inflation of the anchoring balloon 24 within the bladder. As the prostate is located immediately proximal to the bladder neck BN, by spacing the distal end of the energy delivery region very close to the proximal end of the balloon, the delivery region can be properly located, typically being spaced by a distance in the range from 0 mm to 5 mm, preferably from 1 mm to 3 mm from the bladder neck. After the anchoring balloon 24 has been inflated, light and high fluid energy can be delivered into the prostate for debulking as shown by the arrows in FIG. 2, while simultaneously removing the debulked/destroyed tissue and residual fluid by aspiration, typically at both ends of the window, as shown by the arrows 49 in FIG. 3C. Alternatively, the prostate (urethra) can be insufflated or flushed at a pressure greater than that of the aspiration (exhaust) system to enhance tissue and debris collection. Once the energy has been delivered for a time and over a desired surface region, the energy region can be stopped.

As shown in FIG. 3C, the inner fluid delivery tube 35 may be axially translated and/or rotated in order to sweep the fluid/coherent light stream 47 over the interior of the urethra within the prostate P. The energy carried by the fluid/light stream both ablates the prostatic tissue and cauterizes the tissue to limit bleeding after debulking. Once a sufficient volume of tissue has been removed, the fluid stream and light source may be turned off, the balloon 24 deflated, the catheter 10 removed from the urethra.

Referring now to FIGS. 4A-4E, a device 60 constructed in accordance with the principles of the present invention comprises a central shaft 62 having a window 64 near a distal end thereof. A hypotube 66 is carried in a proximal bushing 68 (FIG. 4A) and a threaded region 70 of the hypotube 66 is received within internal threads of the bushing 68. Thus, rotation of the hypotube can axially advance and retract the hypotube relative to the bushing and central shaft 62. Typically, rotation and axial movement of the hypotube 66 relative to the bushing 68 and central shaft 62 is achieved by separately controlling the axial and rotational movement of the hypotube, thereby obviating the need for internal threads and allowing for more versatility of movement within the window 64.

The hypotube 66 carries a laser fiber 72 and includes a lumen 74 which can receive and deliver a water or other fluid jet as will be described in more detail below. The central shaft 62 further includes a balloon inflation lumen 76 and lumen 78 for the suction removal of ablated tissue.

Figure 4A:
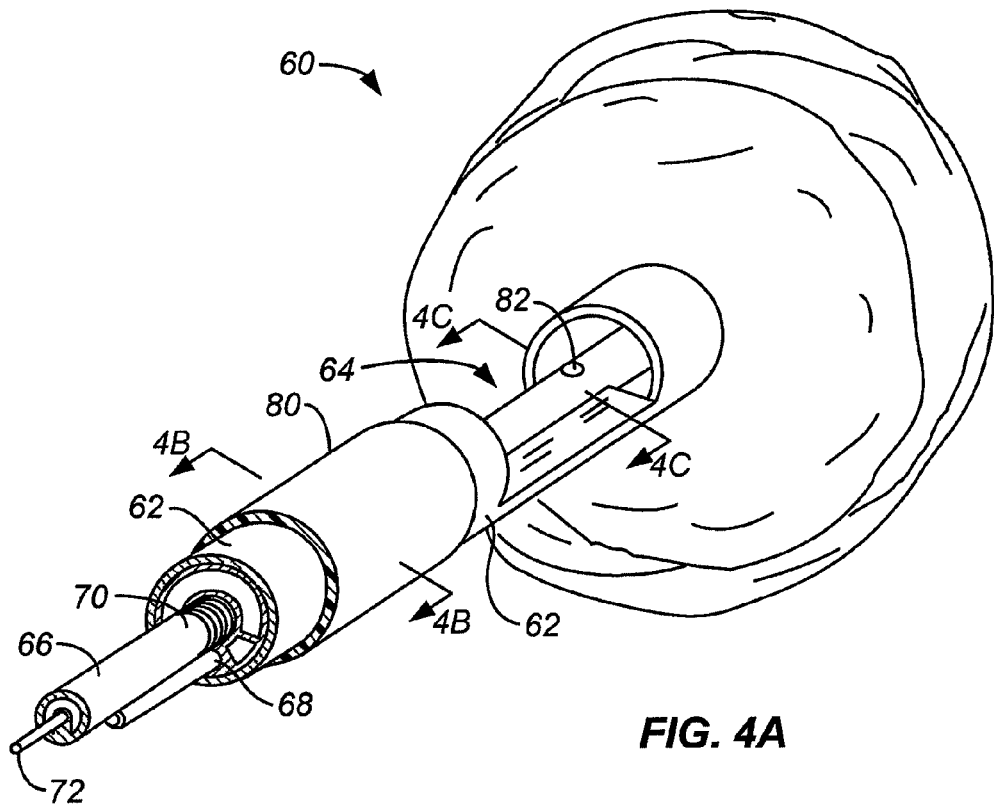
Figure 4B:
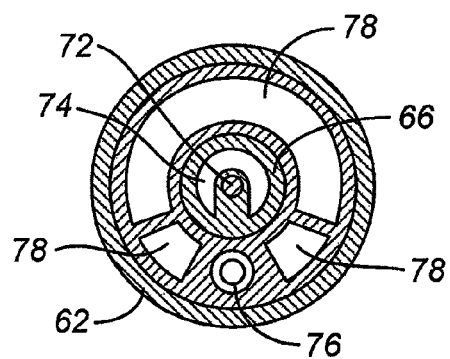
Figure 4C:
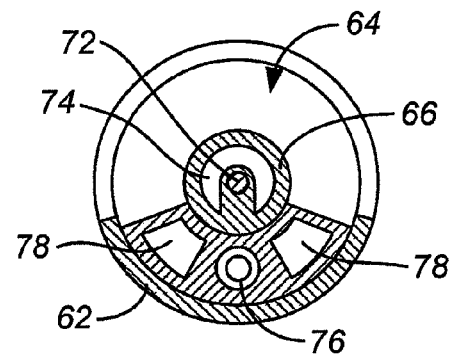

When introduced through the urethra, the device 60 will typically be covered by a sheath 80 as illustrated in FIG. 4D (only a portion of the sheath 80 is shown in FIG. 4A). When fully covered with sheath 80, the window 66 is protected so that it reduces scraping and injury to the urethra as the device is advanced.

Once in place, the sheath 80 will be retracted, exposing the window, as illustrated in FIG. 4E. The hypotube 66 may then be rotated and advanced and/or retracted so that the fluid stream FS which carries the optical energy may be delivered through the delivery port 82. Additionally, a balloon 84 may be inflated in order to anchor the device 60 within the bladder as previously described.

Figure 5:
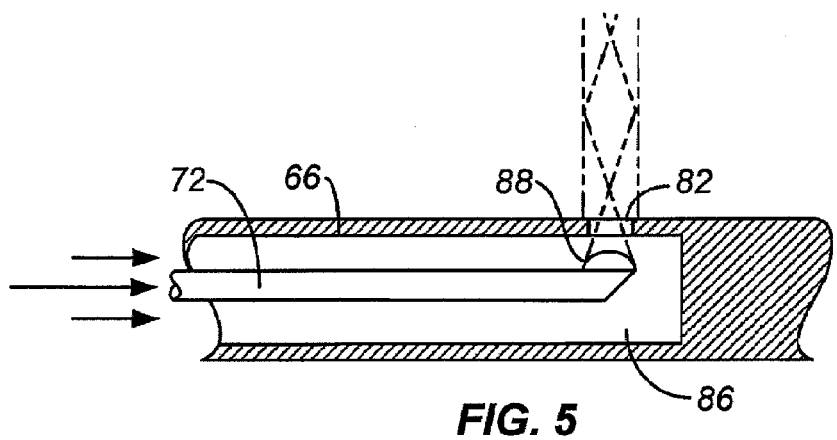
FIG. 5 is a detailed, cross-sectional view of a portion of the rotating and reciprocating fluid and light delivery mechanism of FIGS. 4A-4E.
Figure 6:
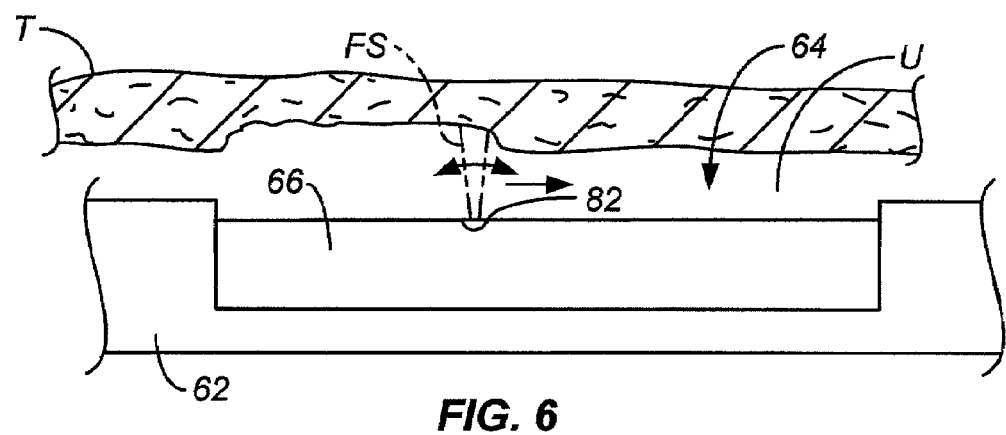
FIG. 6 illustrates use of the device of FIGS. 4A-4E in debulking tissue.

The fiberoptic wave guide 72 is positioned within a lumen 86 of the hypotube 66, as best seen in FIG. 5. Fluid may be delivered through the lumen, surrounding the laser fiber 72 and ejected through the delivery port 82 in a lateral direction. Optical energy delivered through fiber 72 is also reflected laterally and focused by optional lens 88 so that the light is carried by the fluid with internal reflection, as described previously. In use, the hypotube 66 is axially translated within the window 64, as shown in FIG. 6. A fluid stream FS which carries the optical energy is thus directed radially outwardly and against a wall of the body lumen, for example of the urethra U. The energized fluid stream FS is able to ablate a desired depth of tissue T, where the depth can be controlled by the amount of energy delivered and the dwell time or scan time of the fluid stream FS against the tissue.

Figure 7:
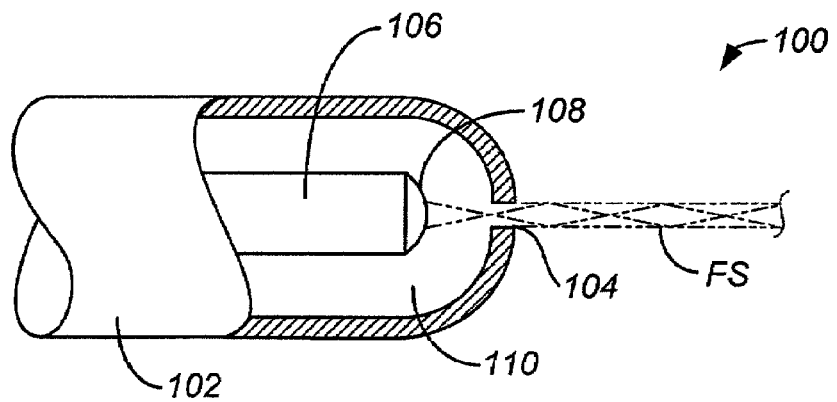
FIG. 7 is a schematic illustration of a device constructed in accordance with the present invention suitable for performing tissue cutting or other procedures where an axial pressurized liquid stream is delivered from a distal tip of the device and carries focused coherent light from a waveguide.
Figure 10:
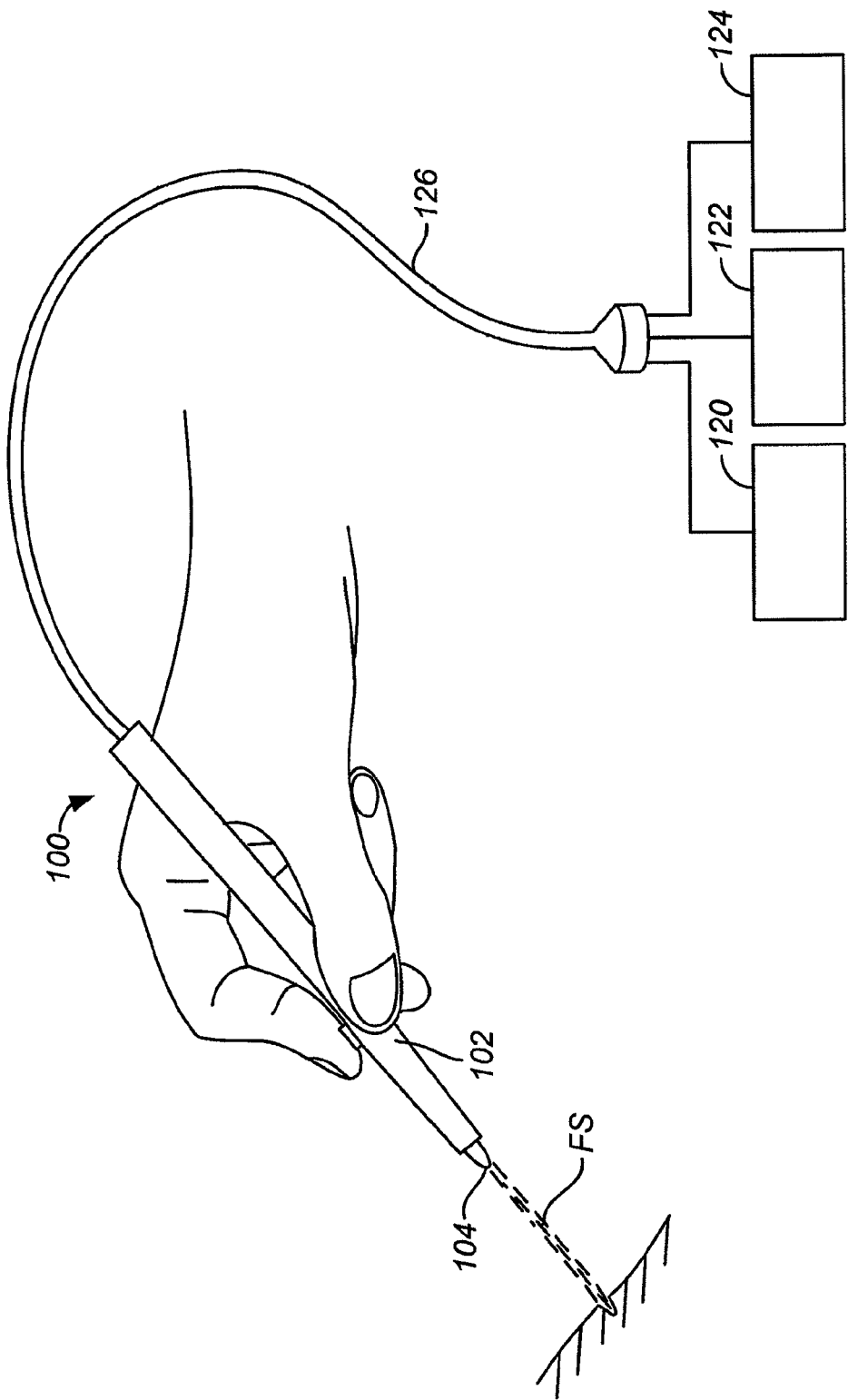
FIG. 10 illustrates use of the device of FIG. 7 as a scalpel for cutting tissue.

As shown in FIG. 7, a handheld device 100 may comprise a shaft 102 having a distal end with a nozzle 104 oriented to deliver a pressurized fluid in an axial stream or water jet FS. A laser fiber 106 is disposed axially within the shaft 102 and terminates in a lens 108 which focuses light into the axial water jet FS. Water or other fluid is delivered under pressure in an annular region 110 of the shaft 102 which surrounds the laser fiber 106 and is enclosed by an outer perimeter of the shaft. The handheld device 100 is capable of delivering an axial water jet or other pressurized fluid stream and is useful for the manual cutting of tissue or bone, as shown in FIG. 10. The handheld device 100 is connected to a pressurized fluid source 120, a light source 122, and control circuitry 124, typically by a connecting cord 126. The user can thus control the fluid pressure, the amount of light energy being introduced into the fluid stream, movement of the nozzle (velocity, direction, limits, etc.) and other aspects of the treatment protocol in addition to the axial and rotational movement parameters using the control circuitry. Optionally, although not illustrated, the nozzle 104 will be adjustable in order to adjust the width and focus of the fluid stream FS in order to allow further flexibility for the treatment. When used for cutting tissue, it can be manipulated much as a scalpel.

Figure 8:
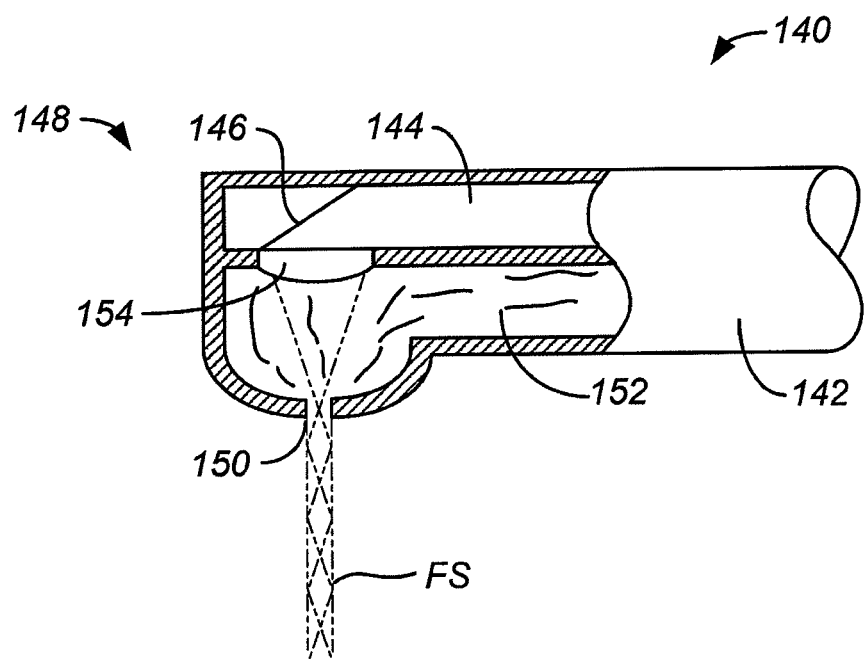
FIG. 8 illustrates another handheld device constructed in accordance with the principles of the present invention, where the pressurized liquid stream carrying the coherent light is directed laterally from the shaft of the device.
Figure 11:
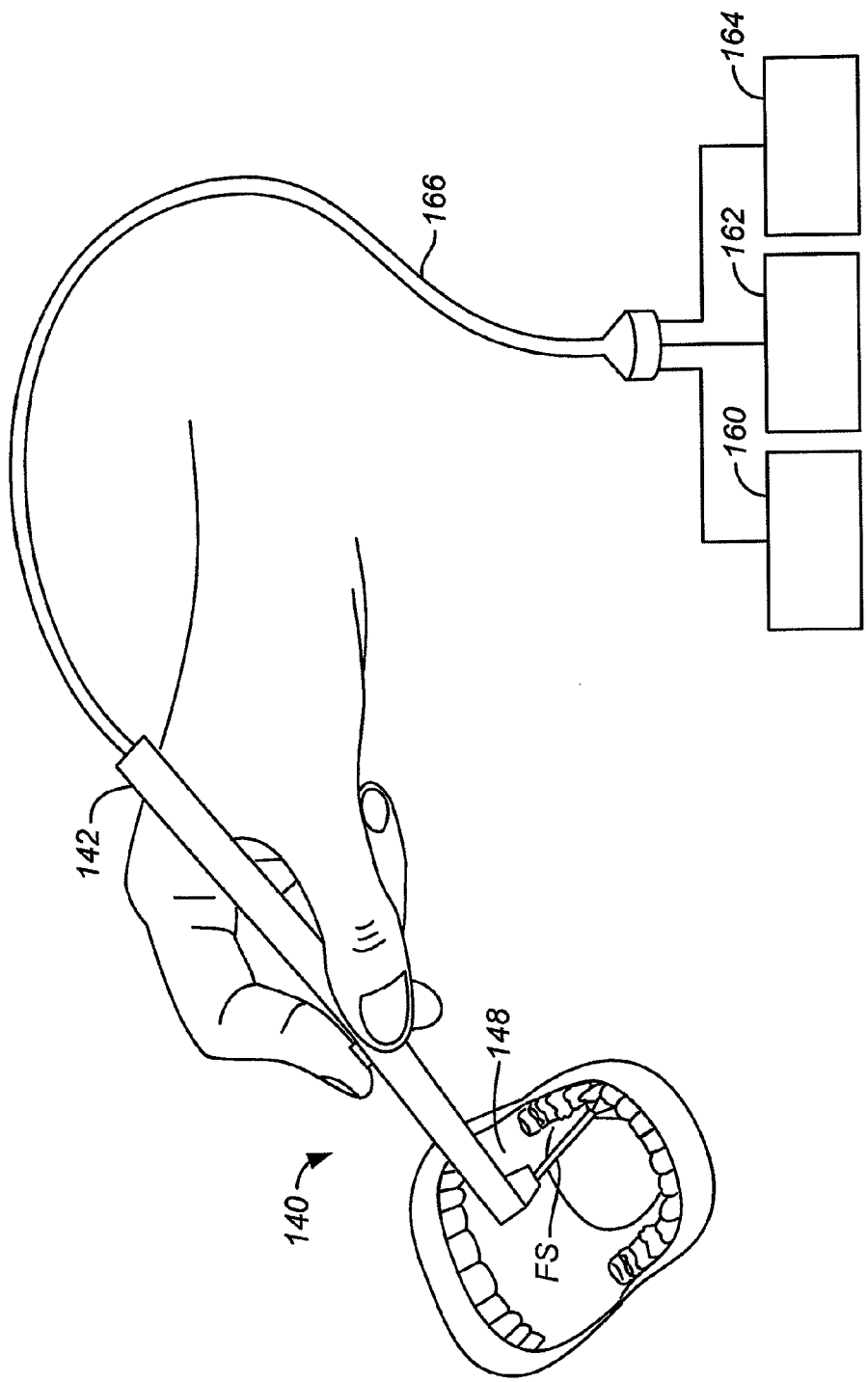
FIG. 11 illustrates the use of the device of FIG. 8 for drilling a tooth.

FIG. 8 illustrates another handheld device 140 where a principle difference with the device of FIG. 7 is that the water jet or other pressurized fluid stream FS is directed in a lateral direction from shaft 142, illustrated as a right angle relative to an axis of the shaft 142. Light is delivered through a laser fiber 144 and reflected, typically by an air mirror 146, or side firing optical fiber, laterally near a distal end 148 of the shaft 142 so that light enters the lateral water jet or other pressurized fluid stream FS, as described previously. The pressurized fluid stream FS is created through a fixed or adjustable nozzle 150 on the side of the shaft 142, where the fluid is delivered under pressure through a lumen or other conduit 152 formed within the shaft 142. As with previous embodiments, a focusing lens 154 is optionally provided to deliver the coherent light from the laser fiber 144 into the water jet or other pressurized fluid stream FS. The device of FIG. 8 may be used for a variety of procedures, such as tooth drilling as illustrated in FIG. 11. The lateral flow handheld device 140 can be held and manipulated by the dentist in a manner similar to conventional dental drills. The distal end 148 of the shaft will be held in the mouth so that the stream FS is directed against the dental surface to be treated. The shaft 142, laser fiber 144, and flow lumen 152 will be connected to a water or other fluid source 160, a suitable laser light source 162, and control circuitry 164 by connecting cable 166.

Figure 9:
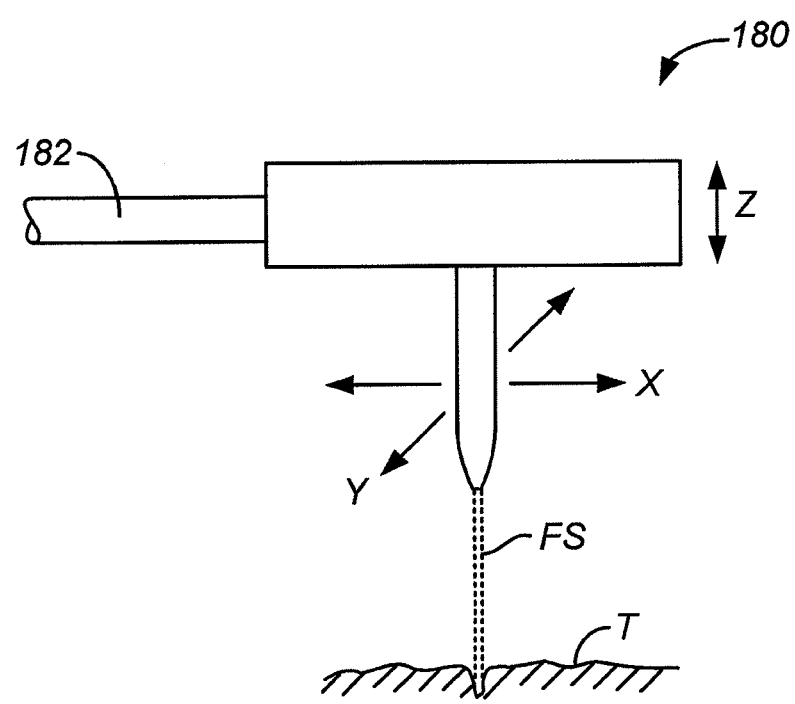
FIG. 9 illustrates a robotically deployed pressurized fluid/coherent light delivery mechanism.

As illustrated in FIG. 9, a scalpel-type device 180 may be attached to a programmable machine arm 182 so that the systems can be used in robotic or other automatic, programmable systems. The programmable machine arm 182 may be suspended over tissue T to be treated, and the water jet or other pressurized fluid stream FS carrying the coherent light is used to cut or incise the tissue, as illustrated. The programmable machine arm may be moved in any of the X, Y, and/or Z directions, where the control is provided by computer or by a manual control system, for example, guided by a joystick or other manipulator.

Figure 12:
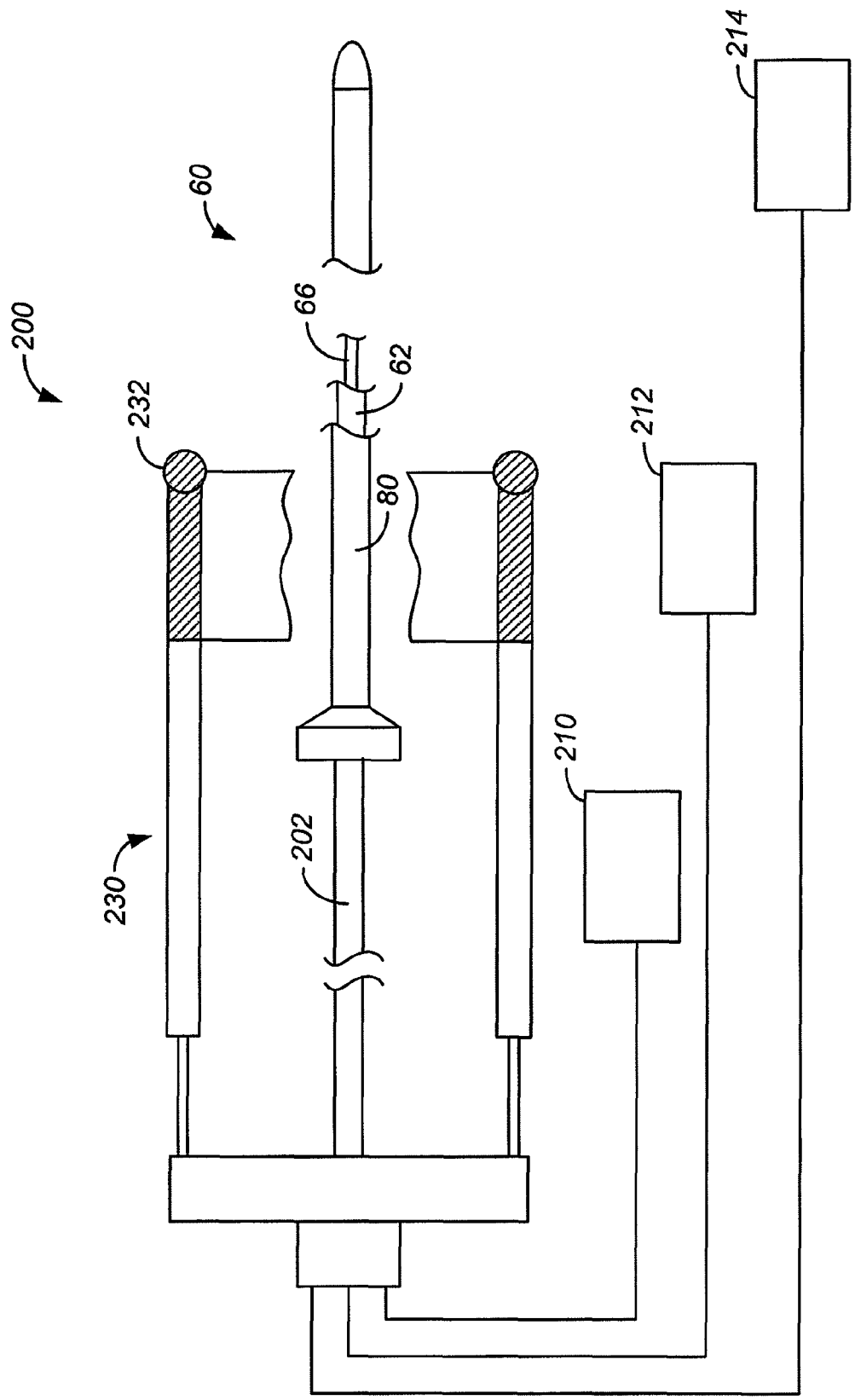
FIG. 12 illustrates a system for deploying a tissue debulking device similar to that illustrated in FIGS. 4A-4E and including a tissue stabilization sheath and schematically illustrating the various drive mechanisms in accordance with the principles of the present invention.

A system 200 for the automatic deployment of the light fluid delivery device 60 of FIGS. 4A-4E is illustrated in FIG. 12. The central shaft 62, hypotube 66, and sheath 80 of the device are connected to a control shaft 202 which in turn is connected to a base unit 204 which includes motors and control circuitry (not shown) for controlling the relative movements of the shaft, hypotube, and sheath. The base unit 204 in turn will be connected to a pressurized fluid source 210, a laser or other optical energy source 212, and an external console or controller 214 which provides an interface for programming and/or manipulating the device 60. In addition to the device 60, the system 200 may include an external anchor frame 230 which can be automatically (or manually) advanced and retracted coaxially over the device 60. The anchor frame 230 typically includes an atraumatic ring 232 for engaging and anchoring the system against tissue after the device has been introduced and the balloon expanded to allow the device to be tensioned.

The apparatus and systems of the present invention may include a number of other optional features. For example, blades or other cutting elements could be included within the waste lumen(s) 78 of the device 60 in order to macerate tissue and other debris as it is being aspirated/evacuated and removed. The device 60 or any of the other configurations of the present invention may optionally be provided with imaging and illumination fibers, cameras, or the like, in order to provide for visual monitoring during the procedure. Optical fibers or cameras may be placed anywhere on the device, optionally within the treatment windows as described before. Means may be provided for keeping the cameras, fibers, lenses, or the like, clean so that good images may be obtained. In all of the above embodiments, instead of employing mirrors, the light may be directed into the fluid stream by bending the light fiber. Additionally, depending on the size of the light fiber and proximity of the fluid nozzle, a focusing lens may or may not be necessary.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for modifying a tissue, said method comprising:
   providing a shaft, a lumen and a distal end, the lumen extending to a nozzle positioned near the distal end of the shaft, the nozzle comprising a restriction sized smaller than the lumen, wherein an optical fiber extends along the shaft to a light emitting end located within the lumen near the distal end of the shaft and the restriction;
   generating a pressurized stream of a light transmissive liquid medium with the restriction sized smaller than the lumen;
   coupling a source of coherent light into the stream of the light transmissive medium with the optical fiber, wherein the light emitting end of the optical fiber and the restriction are arranged near the distal end with the light emitting end spaced from the restriction to focus coherent light into the restriction and the fluid stream emanating from the restriction and wherein said coherent light is transmitted through said stream by total internal reflection; and
   directing the stream from the restriction to the tissue.

2. A method as in claim 1, wherein the liquid stream is generated by passing the liquid medium under pressure through a nozzle with a diameter in the range from 0.01 mm to 1 mm.

3. A method as in claim 2, wherein the pressure is in the range from 1 psi to 1000 psi.

4. A method as in claim 3, wherein the coherent light has a power level in the range from 10 mW to 40 W.

5. A method as in claim 1, wherein the tissue is luminar tissue and the stream is directed radially outward from the lumen.

6. A method as in claim 5, further comprising positioning a probe within the lumen, directing the pressurized stream of the light transmissive liquid medium radially outwardly from a nozzle of the probe, and focusing the coherent light within the stream of liquid medium as the stream is directed at the tissue.

7. A method as in claim 6, wherein the nozzle has a diameter in the range from 0.01 to 1 mm, the pressure is in the range from 1 psi to 1000 psi, and the coherent light has a power from 10 mW to 40 W.

8. A method as in claim 6, wherein the nozzle has a diameter in the range from 0.01 to 1 mm, the pressure is in the range from 1 psi to 1000 psi, and the coherent light has a power from 10 mW to 40 W.

9. A method as in claim 6, wherein the nozzle has an area in the range from 0.01 to 1 mm, the pressure is in the range from 1 psi to 1000 psi, and the coherent light has a power from 10 mW to 40 W.

10. A method as in claim 1, wherein the tissue is soft tissue and the stream is directed at a line to cut the tissue.

11. A method as in claim 1, wherein the tissue comprises a tooth or bone and the stream is directed to drill into the tooth or cut through bone and cartilage.

12. A method as in claim 1, wherein the coherent light is transmitted from the restriction to the tissue with substantially constant power density through the fluid stream in order to decrease distance control.

13. A method as in claim 1, wherein the coherent light from the light emitting tip is focused into the restriction with one or more of a curved mirror or a lens.

14. A method as in claim 1, wherein the light and the pressurized stream converge within the restriction to provide a confluence of the coherent light and the pressurized stream within the restriction.

15. A method as in claim 1, wherein the light is deflected away from an axis near the distal end to concentrate the coherent light within the restriction.

16. A system for delivering laser energy to tissue, said system comprising:
   a probe comprising a shaft having a lumen and a distal end;
   a nozzle positioned near the distal end for emitting a pressurized stream of a light transmissive fluid outward from the probe, the lumen extending to the nozzle, the nozzle comprising a restriction sized smaller than the lumen positioned near the distal end;
   an optical fiber positioned within the lumen for transmitting coherent light, the optical fiber comprising a light emitting end; and
   wherein the light emitting end of the optical fiber and the restriction are arranged near the distal end with the light emitting end spaced from the restriction to focus coherent light into the restriction when the fluid stream emanates from the restriction and to transmit the coherent light through the stream of light transmissive fluid by total internal reflection.

17. A system as in claim 16, further comprising a pump for delivering the light transmissive fluid to the nozzle at a pressure from 1 psi to 1000 psi.

18. A system as in claim 17, wherein the nozzle has a diameter in the range from 0.01 mm to 1 mm.

19. A system as in claim 18, wherein the probe comprises an outer tube having an axial lumen and an inner fluid delivery tube reciprocably mounted in the axial lumen, wherein the central axial passage is disposed in the inner fluid delivery tube and the waveguide is disposed in the central axial passage.

20. A system as in claim 19, wherein the nozzle is disposed to emit the stream of light transmissive fluid laterally through a window in the outer tube.

21. A system as in claim 17, wherein the probe has at least one central axial passage for delivering the light transmissive fluid to the nozzle.

22. A system as in claim 16, further comprising a laser source for delivering coherent light to the waveguide at a power level in the range from 10 mW to 40 W.

23. A system as in claim 16, wherein the probe is adapted to be advanced through luminal surfaces or lumens.

24. A system as in claim 23, wherein the nozzle emits the stream of light transmissive fluid at a pressure in the range from 1 psi to 1000 psi and at a stream diameter from 0.01 mm to 1 mm and wherein the coherent light is transmitted at a power level in the range from 10 mW to 40 W.

25. A system as in claim 16, wherein the probe is hand held and adapted to deliver energy to cut soft tissue.

26. A system as in claim 25, wherein the probe comprises a shaft having an axis.

27. A system as in claim 26, wherein the nozzle is oriented to deliver the stream in an axial direction relative to the shaft.

28. A system as in claim 26, wherein the nozzle is oriented to deliver the stream in a lateral direction relative to the shaft.

29. A system as in claim 25, wherein the nozzle emits the stream of light transmissive fluid at a pressure in the range from 1 psi to 1000 psi and at a stream diameter from 0.01 mm to 1 mm and wherein the coherent light is transmitted at a power level in the range from 10 mW to 40 W.

30. A system as in claim 16, wherein the probe is hand held and adapted to deliver energy to drill teeth or cut through bone and cartilage.

31. A system as in claim 30, wherein the probe comprises a shaft having an axis.

32. A system as in claim 31, wherein the nozzle is oriented to deliver the stream in a lateral direction relative to the shaft.

33. A system as in claim 30, wherein the nozzle emits the stream of light transmissive fluid at a pressure in the range from 1 psi to 1000 psi and at a stream diameter from 0.01 mm to 1 mm and wherein the coherent light is transmitted at a power level in the range from 10 mW to 40 W.

34. A system as in claim 16, further comprising an anchor frame disposed coaxially over the probe and having a distal end adapted to engage a tissue surface when the probe is introduced into a body lumen.

35. A system as in claim 16, wherein the light emitting tip and the restriction are arranged to transmit the coherent light from the restriction to the tissue with a substantially constant power density through the fluid stream in order to decrease distance control.

36. A system as in claim 16, further comprising one or more of a curved mirror or a lens positioned to focus light from the light emitting end into the restriction.

37. A system as in claim 16, wherein the light emitting end and the restriction are arranged to provide a confluence of the coherent light and the pressurized stream within the restriction.

38. A system as in claim 16, wherein the light emitting end and the restriction are arranged to concentrate the coherent light in the restriction with deflection of the coherent light near the distal end.

* * * * *

UNITED STATES PATENT AND TRADEMARK OFFICE
CERTIFICATE OF CORRECTION

Page 1 of 1

PATENT NO. : 8,814,921 B2
APPLICATION NO. : 12/399585
DATED : August 26, 2014
INVENTOR(S) : Aljuri et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1028 days.

Signed and Sealed this
Eighth Day of September, 2015

Michelle K. Lee
*Director of the United States Patent and Trademark Office*